United States Patent
Rey et al.

(10) Patent No.: US 10,718,003 B2
(45) Date of Patent: Jul. 21, 2020

(54) DETECTING AN ANALYTE IN A FLASH AND GLOW REACTION

(71) Applicant: Roche Molecular Systems, Inc., Pleasanton, CA (US)

(72) Inventors: Diego Ariel Rey, Palo Alto, CA (US); Paul Hayter, Mountain View, CA (US); Manoj Sharma, Milpitas, CA (US); Nick Reinig, Los Altos, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 613 days.

(21) Appl. No.: 15/384,207

(22) Filed: Dec. 19, 2016

(65) Prior Publication Data

US 2017/0191111 A1 Jul. 6, 2017

Related U.S. Application Data

(60) Provisional application No. 62/273,845, filed on Dec. 31, 2015.

(51) Int. Cl.
*C12Q 1/14* (2006.01)
*G16C 20/70* (2019.01)

(52) U.S. Cl.
CPC ............ *C12Q 1/14* (2013.01); *G16C 20/70* (2019.02)

(58) Field of Classification Search
CPC . A61B 5/14546; A61B 5/0261; A61B 5/7203; A61B 5/7221; A61B 5/7275; A61B 5/7278; A61B 5/7282; A61B 5/742; A61B 5/7225; A61B 5/726; C12Q 1/6851; C12Q 2537/165; C12Q 1/42; C12Q 1/48; C12Q 1/50; C12Q 2600/158; C12Q 2600/118; C12Q 2600/112; C12Q 1/6888; C12Q 1/689; C12Q 2521/331; C12Q 1/02; C12Q 1/14; C12Q 1/6827; C12Q 1/68;

(Continued)

(56) References Cited

U.S. PATENT DOCUMENTS

2005/0207943 A1 9/2005 Puzey
2006/0008809 A1 1/2006 Li et al.

(Continued)

FOREIGN PATENT DOCUMENTS

EP 1798542 A1 6/2007

OTHER PUBLICATIONS

International Search Report dated May 2, 2017 in Application No. PCT/EP2016/082880, 13 pages.

*Primary Examiner* — Mary K Zeman
(74) *Attorney, Agent, or Firm* — Kilpatrick Townsend and Stockton LLP

(57) ABSTRACT

Accurate measurements of the presence or absence of an analyte (e.g., MRSA) in a sample are provided. For example, the sample can be subjected to an activation reagent (potentially after an initial reagent has already been added), which can cause a flash signal that increases and then decreases over time. Signal data points can be measured from the flash signal using a detector. A quadratic regression function that fits the signal data points can be determined. An accuracy of the quadratic fit can be determined, as well as a signal-to-background ratio. A difference between a signal-to-background term and an accuracy term can be used as a score that is compared to a threshold to determine whether the analyte is present in the sample.

31 Claims, 9 Drawing Sheets

(58) Field of Classification Search
CPC .. C12Q 1/6883; C12Q 1/6816; C12Q 1/6825; C12Q 2565/30; G01N 30/74; G01N 21/01; G01N 21/359; G01N 21/41; G01N 21/76; G01N 33/582; G01N 2800/60; G01N 33/6893; G01N 2333/705; G01N 2800/56; G01N 21/6428; G01N 33/6803; G01N 33/6848; G01N 2800/50; G01N 30/8675; G01N 30/88; G01N 33/533; G01R 33/31; G01R 33/46; G01R 33/4625; G01R 33/465; G06F 3/011; G06F 17/5081; G06F 3/017; G06F 3/0304; G06F 19/00; G06F 19/10; G06F 19/24; G06F 3/03547; G06F 3/041; G06F 3/122; G06F 3/123; G06F 3/1284; G06F 3/1285; G06F 9/4411; G06F 19/18; G06F 3/012; G06F 3/015; G06F 3/016; G06F 19/22; G06F 19/707; G06F 3/038; G06F 3/0383; G06T 7/0012; G06T 7/136; G16H 50/30; G05B 2219/32287; G05B 2219/35001; G05B 2219/37337; G05B 23/0221; G05B 23/024; G05B 19/042; G06K 9/62; G06K 9/6262; G06N 20/00; G06N 3/02; H04B 17/309; H04B 17/318; H04B 17/345; H04W 4/38; C12M 41/32; C12M 41/48; G16B 20/00; G16B 20/10; G16B 30/00; G16B 25/00; G16B 30/10; G16B 40/00

See application file for complete search history.

(56) References Cited

U.S. PATENT DOCUMENTS

| | | |
|---|---|---|
| 2010/0100336 A1 | 4/2010 | Wright |
| 2015/0247190 A1* | 9/2015 | Ismagilov ............ C12Q 1/6851 506/9 |

* cited by examiner

| | Sensitivity | 95% C.I. | | Specificity | 95% C.I. | |
|---|---|---|---|---|---|---|
| S/B-quad | 90.24% | 77.45% | 96.14% | 99.29% | 96.09% | 99.87% |
| Average Max RLU | 100.00% | 90.82% | 100.00% | 75.89% | 68.20% | 82.20% |
| Average Max RLU + 1STD | 100.00% | 90.36% | 100.00% | 91.49% | 85.71% | 95.06% |
| Average Max RLU + 2STD | 92.31% | 79.68% | 97.35% | 95.74% | 91.03% | 98.04% |
| Average Max RLU + 3STD | 24.65% | 18.29% | 32.34% | 95.74% | 91.03% | 98.04% |

| PPV | 95% C.I. | | NPV | 95% C.I. | | Agreement | 95% C.I. | |
|---|---|---|---|---|---|---|---|---|
| 97.4% | 86.5% | 99.5% | 97.2% | 93.1% | 98.9% | 97.3% | 93.7% | 98.8% |
| 52.8% | 41.4% | 63.9% | 100.0% | 96.5% | 100.0% | 81.0% | 74.6% | 86.1% |
| 75.0% | 61.2% | 85.1% | 100.0% | 97.1% | 100.0% | 93.2% | 88.5% | 96.1% |
| 85.7% | 72.2% | 93.3% | 97.8% | 93.8% | 99.3% | 95.0% | 90.8% | 97.3% |
| 85.4% | 71.6% | 93.1% | 55.8% | 49.5% | 61.9% | 60.1% | 54.3% | 65.6% |

FIG. 7

DETECTING AN ANALYTE IN A FLASH AND GLOW REACTION

CROSS-REFERENCES TO RELATED APPLICATIONS

The present application claims priority from and is a non-provisional application of U.S. Provisional Application No. 62/273,845, entitled "Detecting An Analyte In A Flash And Glow Reaction" filed Dec. 31, 2015, the entire contents of which are herein incorporated by reference for all purposes.

BACKGROUND

In many applications for chemometrics etc., indirect measurements and direct measurements (e.g. concentrations) of samples are used to develop a calibration curve, which can be used to predict a direct measurement from an indirect measurement. In some cases, Y can be one or more indirect measurements (e.g., multivariate data) and X can be the direct measurement. A calibration curve can be developed between X and Y, and normality assumptions made for the distributions of X and Y.

In many instances, the direct variable X is continuous, and residual analysis can be used to determine the calibration curve. Such predictions are not applicable to the situation where X is a class variable, i.e. X corresponds to two (binary) or more classes. In many applications, the direct measurements could be a class variable; and in this case, logistic regression or discriminant analysis can be used for predicting the class based upon the indirect measurement and the relationship between indirect measurements and direct measurements.

In logistic regression, the classification is assigned on the basis of likelihood/probability of being in each class. The normality assumption is made for the indirect measurements, and classification is achieved in terms of odds ratio computation.

In discriminant analysis, a linear distance of indirect measurements from different classes is calculated, and the class is assigned on the basis of a minimum distance. In this case too, a normality assumption is made for the distribution of indirect measurements. In certain applications, it is of interest to discriminate classes near a cutoff from one class to another, e.g., in the determination of the presence or absence of an analyte in a sample.

But, such a discrimination can be difficult to perform accurately, thereby diminishing the sensitivity and specificity. Such a discrimination can be even more difficult to determine accurately when there are multiple indirect measurements over time, as can happen in flash reactions (e.g., involving methicillin-resistant *Staphylococcus aureus*, MRSA).

BRIEF SUMMARY

Embodiments can provide accurate measurements of the presence or absence of an analyte (e.g., MRSA) in a sample. For example, the sample can be subjected to an activation reagent (potentially after an initial reagent has already been added), which can cause a flash signal that increases and then decreases over time. Signal data points can be measured from the flash signal using a detector. Embodiments can determine a regression function that fits the signal data points. An accuracy term of the regression function can be determined, as well as a signal-to-background term. A difference between a signal-to-background term and an accuracy term can be used as a score that is compared to a threshold to determine whether the analyte is present in the sample.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 7 is a table 700 showing a comparison of accuracy results between use of maximum signal vs scores according to embodiments of the present invention.

DETAILED DESCRIPTION

Figure 1:
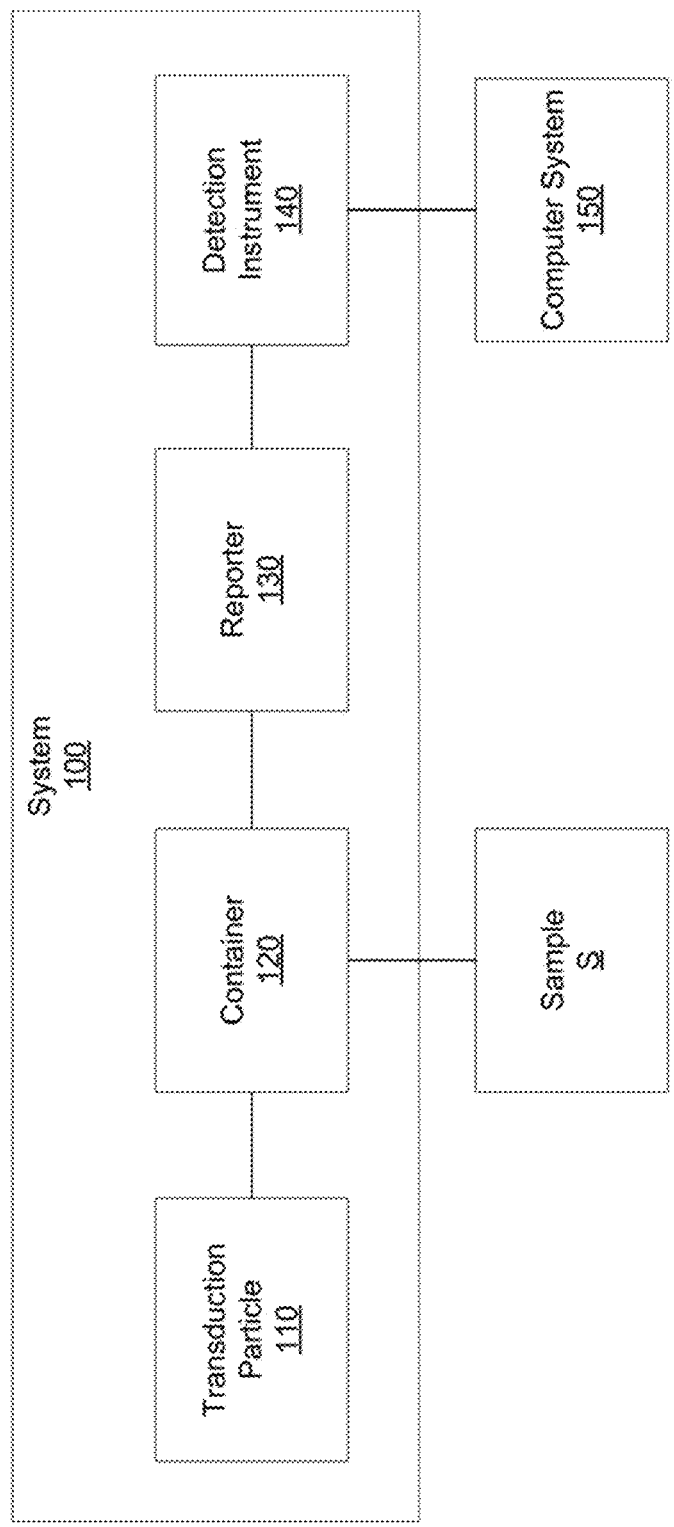
FIG. 1 is a block diagram of a system for bacteria identification according to embodiments.

It can be difficult to discriminate between methicillin-resistant *Staphylococcus aureus* (MRSA) and methicillin-susceptible *Staphylococcus aureus* (MSSA). Some tests for determining whether MRSA is present in a sample involve a flash reaction, e.g., as described in PCT publications WO2014/160418, WO2014/164768, and WO2015/164746. Such flash signals can be detected by a detector, e.g., as signal data points detected at various times. Such flash signals can occur in various reactions of various analytes. Examples of analytes include those based on live cell luminescence assays.

However, flash signals occur for both MSSA and MRSA, although there are differences in the flash signals. Embodiments can analyze signal data points at multiple times as part of determining a signal-to-background ratio. The use of multiple signal data points can provide greater accuracy than simply using a maximum value. A regression can also be performed. While a quadratic function may be used for the regression, regressions to other polynomial functions such as the third, fourth, fifth or sixth order could also be used. An accuracy term of the regression fit can be adjusted by subtracting or adding a signal-to-background term to provide a score that can provide high sensitivity and specificity for discriminating between positive and negative samples.

Some embodiments do not need any assumption regarding distribution of indirect measurements, and the classification can optimize an objective function for achieving optimal sensitivity and specificity. Embodiments can provide greater sensitivity and/or specificity (or greater total) over using an average of indirect measurements. Using an average over MRSA and MSSA would not be optimal as several MRSA samples would have very high signal values, while some MRSA samples would have signal values very close to MSSA samples.

I. Flash Reactions

In some embodiments, systems and methods are designed for the detection of an analyte in a sample. The analyte can be detected based on signals resulting from a flash reaction involving the sample and an activation reagent. In one example, a system is designed for detecting the presence of MRSA via a luminescence assay (an example including an activation reagent). The assay can employ a first reagent that causes viable MRSA cells to produce a luminescence signal when activated via a second reagent. A detector (e.g., a photomultiplier tube-based (PMT) detector) is employed for collecting data.

The collected data can be analyzed to distinguish the presence of MRSA from the absence of MRSA based on characteristics of the data collected. The analysis can be performed to provide an accurate measurement of the sample for the presence of the analyte. Parameters of the analysis can be chosen based on reference data from samples known to be positive and negative for MRSA, respectively, such that the results produce a desired sensitivity and specificity with respect to the reference data.

The reference data may be identified as positive/negative for MRSA based on any suitable reference assay, including those accepted as standards. In examples below, the reference data is determined to be known positive/negative for MRSA based on an enriched culture method for MRSA detection as described in FDA Draft Document—Establishing the Performance Characteristics of Nucleic Acid-Based In vitro Diagnostic Devices for the Detection and Differentiation of Methicillin-Resistant *Staphylococcus aureus* (MRSA) and *Staphylococcus aureus* (SA); Issued on Jan. 5, 2011, which is incorporated by reference. Such a test has high accuracy, but is time-consuming and costly to run, and thus not practical in many instances. The collected data may be derived from a variety of sources including contrived samples or clinical samples. For example, clinical sample data from nasal swabs collected for the purpose of MRSA surveillance are used in examples described in later sections.

A. System

In some embodiments, the system described in PCT publication WO 2014/164768 can be employed using the consumable described in PCT publication WO 2015/164746 and running the MRSA assay described in PCT publication WO 2014/160418 that describes the assay and performance; all of which publications are incorporated by reference in their entirety.

Systems, devices and methods for detecting and identifying target cells (e.g., bacteria) or other analyte can include a transduction particle, which can identify and bind to the target cell and deliver into the target cell an engineered nucleotide. As shown in the block diagram of FIG. 1, in some embodiments, a system 100 includes a genetically engineered transduction particle 110, a container 120, a reporter 130, a detection instrument 140, and a computer system 150. The system 100 is configured to manipulate, handle and/or actuate the container 120 and/or the detection instrument 140 such that the transduction particle 110 can, when mixed with a sample S that contains a particular target, produce the reporter 130. In this manner, the system 100 and methods associated therewith can be thought of as a "switchable" assay, meaning that no amount of the reporter 130 is present in the sample until the conditions (e.g., the presence of the target cell) are such that the reporter 130 is produced. Detection instrument 140 can be a photomultiplier tube (PMT). The PMT detects photons from the reactions to provide a signal over time.

The transduction particle 110 can be any suitable particle capable of delivering reporter DNA and/or RNA into a target cell. For example, in some embodiments, the transduction particle can be derived from a bacteriophage, or can be a non-biologically derived vector that is capable of introducing nucleic acid molecules into the target bacteria in the sample S. The transduction particle 110 is further engineered and/or configured to carry an engineered molecule, for example, recombinant DNA, RNA, nucleotide, plasmid, ribozyme, aptamer, and/or protein. In some embodiments, the transduction particle 110 does not contain any DNA from the viral vector (e.g., bacteriophage) from which it was derived. Similarly stated, in some embodiments, the transduction particle is a viral vector devoid of a wild-type DNA capable of exhibiting wild-type viral functions associated with the virus from which the viral vector is derived.

In some embodiments, the transduction particle 110 is incapable of replicating via either the lytic or lysogenic cycle. By eliminating all forms of replication from the transduction particle, the target cells will be maintained (i.e., not destroyed, killed or lysed) during the production of the reporter molecules, thereby improving the accuracy and reliability of the methods used therewith. In particular, because wild-type viral functions of viral particles can exhibit lysogenic replication and require the capability for lytic replication, attempts to suppress the replicative functions (e.g., the lytic cycle) may not provide sufficient certainty that the lytic cycle will not result in some population of assays.

The transduction particle 110 can be characterized by being associated with and/or specific to one or more target cells. Similarly stated, the transduction particle 110 is formulated to bind to and deliver a nucleic acid molecule into the target cell. For example, the transduction particle can be selected, engineered and/or produced to bind to any bacteria, e.g., *Escherichia, Mycobacterium, Staphylococcus, Listeria, Clostridium, Enterococcus, Streptococcus, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter* and *Yersinia*.

The transduction particle 110 can be further produced and/or engineered to contain genes and/or a nucleic acid molecule for expressing a reporter 130 that can be detected (e.g., via the instrument 140). The reporter 130 can be any one of a bacterial luciferase, an eukaryotic luciferase, a fluorescent protein (e.g., GFP, etc.), an enzyme suitable for colorimetric detection (e.g., horseradish peroxidase) a protein suitable for immunodetection (e.g., protein A, etc.), a peptide or peptide tag suitable for immunodetection (e.g., 3.times.FLAG, etc.) and/or a nucleic acid that functions as an aptamer or that exhibits enzymatic activity. More particularly, the transduction particle 110 does not produce the reporter 130 autonomously and/or does not include the reporter 130. Instead, transduction particle 110 is configured to communicate an engineered nucleic acid molecule contained therein into the target cell, e.g., bacteria, such that the engineered nucleic acid molecule uses the natural transcription and translation functions of the bacteria DNA to produce the reporter 130. Thus, the reporter 130 can be thought of as a "switchable" reporter, meaning that no amount of the reporter 130 is present in the sample until the conditions (e.g., the presence of the target cell) are such that the reporter 130 is produced. In this manner, certain methods may involve no washing of non-bound reporter 130, no signal subtraction to account for initial quantities of reporter or the like. Thus, the system 100 and the methods associated therewith allows for the development of a homogeneous assay. Further, no temperature cycling may be required, and heating at a low temperature, for example 37 degrees Celsius, for a short time can be sufficient.

The reporter system formulated to cause the expression of the reporter 130 and any of the reporter systems disclosed herein can be developed for reporting on the presence of viable bacteria and/or target cells by incorporating into the non-replicative transduction particle 110 (or any of the other transduction particles disclosed herein) a reporter molecule under the control of a promoter. When this transduction particle 110 introduces the reporter system into a cell within the host range of the transduction particle 110, the promoter is able to drive the expression of the reporter molecule.

In one embodiment, a MSSA/MRSA reporter assay can be developed and/or performed using any suitable system. In such embodiments, a non-replicative transduction particle (e.g., the transduction particle 110, or the like) is developed from a S. aureus-specific bacteriophage, and the bacterial luciferase genes luxAB under the control of a constitutive promoter are incorporated. When this transduction particle introduces the reporter system into S. aureus, the constitutive promoter can express luxAB suitable for reporting on the presence of a viable S. aureus. If in addition, the antibiotic cefoxitin, or a similar anti-biotic, is also added prior to or simultaneously with mixing the transduction particles with S. aureus cells, if the cells do not contain and express the mecA gene, no luxAB will be expressed in the assay, thus indicating that the cells are MSSA (i.e., sensitive to inhibition by cefoxitin). If, however, the cells do contain and express the mecA gene, luxAB will be expressed in the assay, thus indicating that the cells are MRSA (i.e., resistant to inhibition by cefoxitin).

Although described as being developed for reporting on the presence of viable bacteria, in other embodiments, the reporter 130 and any of the applicable reporter systems can be developed for reporting on the presence of target genes within target bacteria. In this system, a promoter-less reporter gene is placed downstream of a nucleic acid sequence that is homologous to a target gene sequence, and this reporter construct is incorporated into a non-replicative transduction particle. When the transduction particle introduces the reporter construct into a target cell, the reporter gene will not be expressed unless the target cell contains the target gene, and a homologous recombination event integrates the reporter gene within the target gene loci in the target cell such that the reporter gene becomes operatively linked to the target gene promoter within target cell.

In one such embodiment, a MRSA reporter system can be developed by incorporating into a S. aureus-specific non-replicative transduction particle (e.g., the transduction particle 110, the transduction particle 160 or the like) a reporter construct consisting of a nucleic acid sequence that is homologous to the mecA gene upstream of promoter-less bacterial luciferase genes, luxAB. When the transduction particle introduces the reporter construct into a target S. aureus cell, the reporter gene will not be expressed unless the target cell contains the target mecA gene and a homologous recombination event integrates the luxAB genes within the mecA gene loci in the target cell such that the reporter gene becomes operatively linked to the mecA gene promoter within target cell.

In some embodiments, transduction particle 110, the nucleic acid molecule contained within the transduction particle 110 and/or the reporter systems associated therewith can include any of the portions of the recombinant bacteriophages shown and described in U.S. Patent Publication No. 2010/0112549, entitled "Microorganism Detection Method and Apparatus," filed as an International Patent Application on Apr. 18, 2008, which is incorporated herein by reference in its entirety.

The sample S can be any sample that possibly contains the target analyte, for example, human nasal swab, blood, urine, veterinary samples, food samples, and/or environmental samples. In some embodiments, the sample S can be a raw sample as obtained from the source that does not need any preparation, e.g., any separation or washing steps are not needed. Thus, the system 100 and the methods associated therewith can be homogeneous. In some embodiments, the sample S can include a low load of target cell (e.g., nasal swab for MRSA detection). When used with such samples, the system 100 and the methods associated therewith can include a heating and/or incubation period to promote cell replication, which results in higher production of the reporter molecules 130, for example, to generate a signal that is greater than a minimum signal threshold.

In other embodiments, the sample S can have a higher load of target cell (e.g., positive bacterial blood culture). In such cases, cell replication is not needed to produce a positive signal sufficient to identify the target cell. In some such embodiments, the sample can be maintained at a specific condition e.g., maintained at a temperature of greater than or equal to approximately room temperature, 25 degrees Celsius, or 37 degrees Celsius for a predefined time period e.g., less than approximately 4 hours. In such embodiments, the temperature and time period at which the sample S is maintained are such that the quantity of reporter molecules 130 produced is sufficient to generate a measurable signal, independent of cell replication. In such embodiments, the sample can be maintained at the predefined temperature for a longer time period, e.g., 6 hours, 8 hours, up to 18 hours, or even longer.

In some embodiments, the container 120 can contain a first reagent, for example, a bacterial nutrient or growth media (e.g., minimal essential media) and/or suitable buffer (e.g. Amies, PBS, TRIS, HEPES, etc) for maintaining the target cell in a viable state, promoting bacterial cell growth or the like. In some embodiments, an antibiotic, for example, cefoxitin can also be included in the first reagent, for example, when a viable cell assay is intended. A sample S containing the target cell can be added to container 120 followed by addition of the transduction particle 110 to container 120. If the target cells are present, the transduction particle 110 transfers the nucleic acid sequence contained therein into the target cell such that the nucleotide contained in the transduction particle 110 is integrated with the genes of the target cell, e.g., host bacteria.

In some embodiments, the container 120 is configured to fluidically isolate the sample S from a region outside the container 120. In such embodiments, the transduction particle 110 is maintained in fluidic isolation from the sample S before the transduction particle 110 is mixed therein. In some embodiments, the maintaining can include maintaining the sample S for a time period such that the quantity of the plurality of the reporter molecules 130 sufficient to produce the signal is produced independent from target cell replication. As described herein, mixing includes disposing the transduction particle 110 into the sample S while maintaining isolation between the region and the container 120.

In some embodiments, the container 120 can be configured to include an activation reagent that is formulated to react with the reporter molecules 130 to produce, catalyze and/or enhance the production of the signal. For example, the reporter molecule 130 can be luciferase, and the container 120 can be configured to contain an aldehyde reagent formulated to trigger, initiate and/or catalyze a luminescence reaction that can be detected by the production of the signal. In one implementation, a cap of container 120 can contain the activation reagent (e.g., in a blister) that is mixed with the transduced samples via actuation (e.g., popping the blister) by an instrument of system 100.

In various embodiments, the activation reagent can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the container 120 can be configured to maintain the activation reagent in fluidic isolation from sample S before being disposed into the sample S. In this manner the timing of the delivery of the activation reagent into the sample S can be controlled. In some embodiments, the system 100 can include a mechanism for adding the activation reagent at any suitable time and/or in any suitable manner to induce the detectable signal. For example, as described in more detail herein, in some embodiments, the system 100 and/or the container 120 can include a mechanism for conveying an activation reagent into the sample S at a predetermined velocity (or flow rate) to promote the desired level of mixing.

The instrument 140 can be any appropriate instrument to detect the reporter molecule 130 and/or a reaction catalyzed by the reporter molecule 130. For example, the instrument 140 can include optical (e.g. photomultiplier tubes, fluorometers, spectrometers, colorimetric detection on a lateral flow assay, imaging based detection, CCDs, luminescence detectors for detecting bioluminescence, colorimetric or fluorometric microarrays) and/or electrical detection means (e.g. electrochemical amperometric, potentiometric, conductometric, impedrometric, coulometric, and/or any other electrochemical sensors).

Instrument 140 is connected with computer system 150 that analyzes the measured data. The connection can be wired or wireless. As an example of a wireless connection, a removable data storage device at instrument 140 can store the measured data, and the storage device can be removed and inserted into computer system 150.

In some embodiments, the system 100 and/or the methods associated therewith can be configured to be a rapid test that does not require any amplification of the target cells. Using the system 100 and the methods described herein, a relatively small time, for example, 1 hour, 2 hour, 3 hour or 4 hour, up to 18 hours can be needed for the target cell containing the nucleic acid sequence from the transduction particle 110 to produce a sufficient quantity of reporter molecules 130 that can be detected. In some embodiments, the system 100 can be configured to be a closed system after collection of sample S and/or addition of transduction particle 110. Said another way, in some embodiments, the container is maintained in fluidic isolation from the external environment after the addition of the sample S. This can, for example, reduce chances of contamination. As described above, because the system 100 can accommodate raw sample, the system 100 and the methods associated therewith do not require any washing or fluid transfer steps away from the sample S. The system 100 can therefore be easy to operate, be rapid, inexpensive, and be easily automated. In some embodiments, the system 100 can be a platform system that can be configured to operate in various regimes, for example, viable cell reporting, gene reporting, measuring bacterial resistance and/or susceptibility to antibiotics, and/or bacterial toxin detection, etc.

B. Representative Data and Discrimination Problem

Embodiments involve reactions that are of a flash type, and can also include later time region where a glow signal can be seen. Luminescence assays can come in many different types. Luminescence assays are a chemical or enzymatic reaction that use a substrate (activation reagent). In the case of the reporter molecule being bacterial luciferase (LuxAB), the substrate can be a fatty aldehyde (e.g. tridecanal). When the substrate is acted upon by the chemical or enzymatic reaction, light is given off as a by-product. The two main types of luminescence reactions are flash and glow. The flash luminescence reaction can occur quickly, e.g., in a matter of seconds or minutes, giving off a very bright signal. Whereas a glow luminescence assays can last for hours, but are typically not as bright as flash luminescence assays.

As described above, a flash signal can be produced by a sample when an activation reagent activates an analyte or a molecule generated from the analyte (e.g., a reporter molecule generated by bacteria in response to a transduction particle. But, a flash signal can be generated by other similar analytes, as well as the target analyte. For example, a flash signal is generated for MSSA and MRSA. This poses a problem for the discrimination analysis in classifying the sample as positive or negative for the target analyte.

Figure 2:
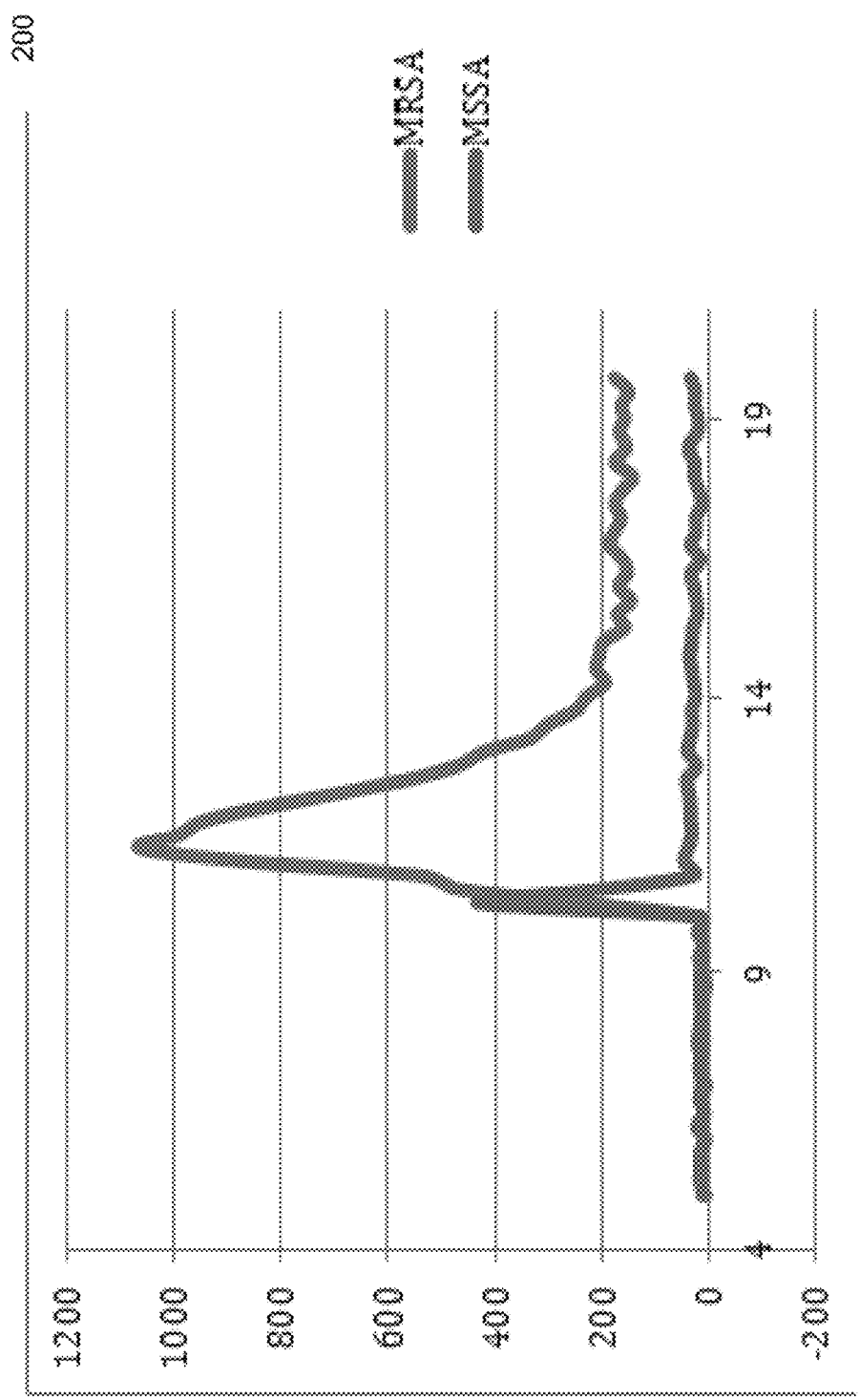
FIG. 2 shows a typical plot 200 of an MRSA signal and an and methicillin-susceptible *Staphylococcus aureus* (MSSA) signal from respective samples according to embodiments of the present invention.

FIG. 2 shows a typical plot 200 of an MRSA signal and an MSSA signal from respective samples according to embodiments of the present invention. The horizontal axis corresponds to time. The vertical axis corresponds to a signal intensity measured by a detector (e.g., a PMT). The measured data includes baseline measurements (data collected before activation reagent is added) and substrate measurements (signal data collected after activation reagent is added). Such signals can result for other analytes besides MRSA.

Although the two signals shown have different maximum values (about 400 for MSSA and about 1050 for MRSA), the maximum values can be much closer. Some MSSA samples can even have a higher maximum signal value (peak) than the maximum for some MRSA samples. Positive signals can have a wide range from very low to high peaks. This noise of similar signals can cause problems for differentiating between positive and negative samples. Thus, just using a maximum value provides too many false positives, e.g., below a desired sensitivity and specificity, as is shown below. Further, the peak can occur at various time points.

To address these difficulties, embodiments can use multiple signal values over time, and not just a single value, so as to analyze a range of kinetics of the signal data. Embodiments can also analyze a curvature of a signal around its peak, as a way to differentiate between positive and negative samples. Such techniques can focus on differentiating signals that are very close to each other so as to provide a desired sensitivity and specificity. Such close data is now discussed.

Figure 3:
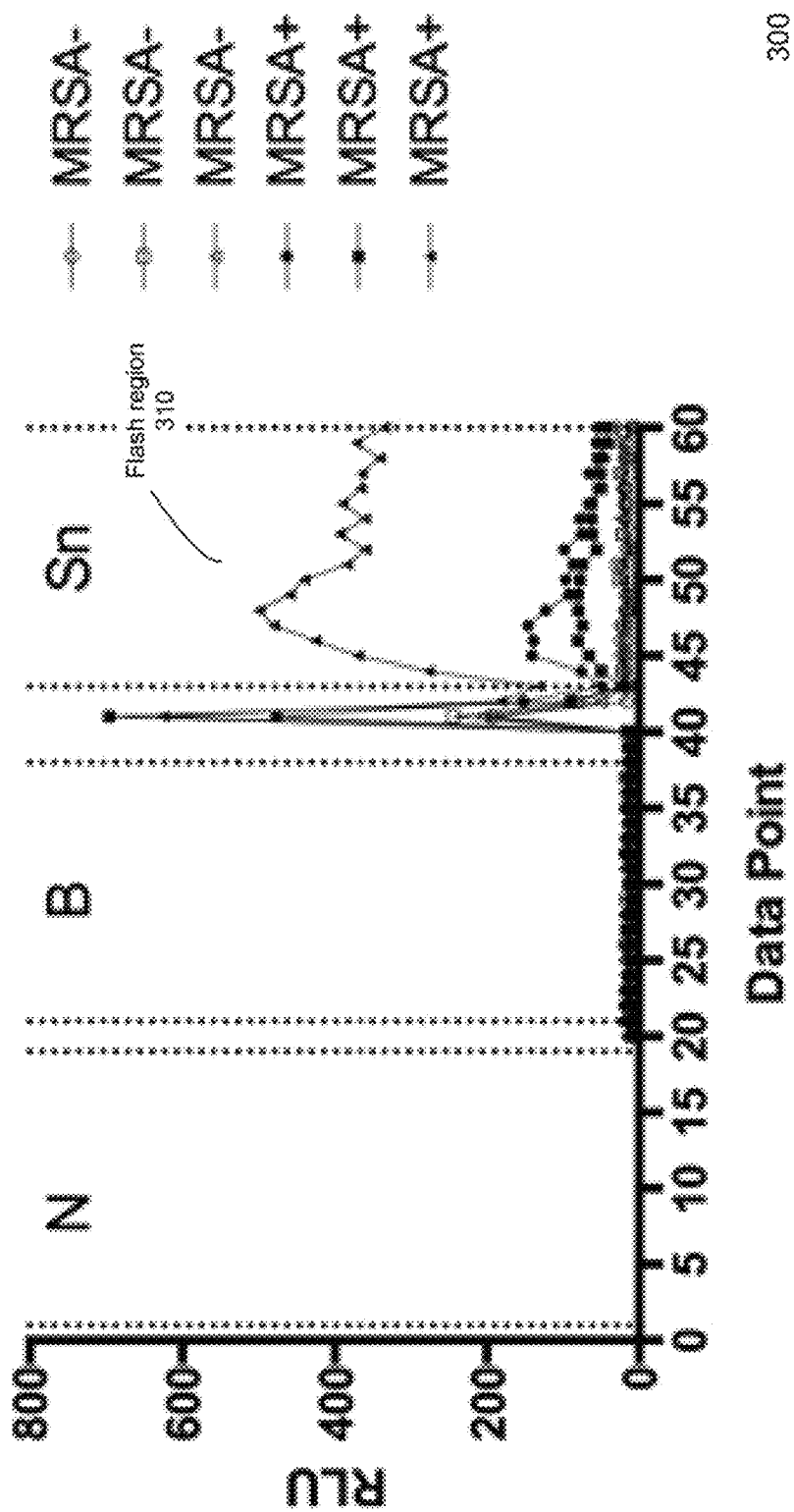
FIG. 3 shows a plot 300 depicting representative data produced from samples that are positive for MRSA and samples that are negative for MRSA according to embodiments of the present invention.

FIG. 3 shows a plot 300 depicting representative data produced from samples that are positive for MRSA and samples that are negative for MRSA according to embodiments of the present invention. The data consists of relative light units (RLU) produced by a PMT vs. time where data is collected from the PMT every quarter second.

In plot 300, N is a 19 data-point region of the data from data point 1 to data point 19. During this time period, a shutter mechanism is blocking the PMT sensor and thus the data produced by the PMT is representative of the noise of the PMT. Next, the shutter is opened and an assay tube is inserted such that the PMT sensor is exposed to the tube during a period of time consisting of a next 20 data-points, specifically data points 20-39. Within this 20-point region, B is an 18 data-point region including data points 21-38 and is considered "background data points" that occur prior to activation of the signal. Finally, the signal is activated at data-point 40. The activation occurs in an 'injection spike' that shows a quick increase and decrease of the signal. This injection spike includes data points 40-42. After the injection spike is a signal Sn, which is a 17 data-point region of the data from data points 43-59. Signal Sn includes a flash region 310 with a peak.

Accordingly, before the activation reagent is injected, there are measurements of a background signal. Pre-signal checks can be made of this background data, as is explained below. For example, the background may be irregular and require the detector to be reset, e.g., container 120 to be re-seated. The data points of the background region can also be used to compute a background (baseline) mean and standard deviation of the background, which can be used in determining a signal-to-background ratio that is used in classifying signals.

In other embodiments, dark count measurements are made every quarter of a second from 0 to 4.75 seconds (e.g., corresponding to region N), where such dark measurement may be ignored for the discrimination analysis. Background measurements can be made every quarter of a second from 5 to 9.75 seconds, and substrate (signal) measurements from 10 to 19.75 seconds. The dark count measurements can be used for checking instrument stability and not used in the discrimination analysis. The background measurements can provide information about instrument-to-instrument differences and can be combined into the statistic (score) with the substrate (signal) data to achieve uniform calibration (e.g., no instrument to instrument calibration may be required).

II. General Flow

In practice, a detection system may produce data that is derived from factors other than the target analyte. These data may be derived from non-specific signal produced by cross-reactive analytes (e.g., MSSA), system noise, aberrant light from external sources, etc. Such data may result in false-positive, false-negative, and null results. Embodiments have been developed to account for such aberrant data to limit false-positive, false-negative, and null results. Besides performing a signal check to discriminate between positive and negative results, pre- and post-signal checks can be applied. For example, pre-signal checks can flag samples to be repositioned into a detector apparatus in attempt to clear the aberration. In some implementations, such a pre-signal check can be done up to three times, and then the measurement will proceed without prejudice. In the case of post-signal checks, flagged samples can be designated as invalid or negative.

Figure 4:
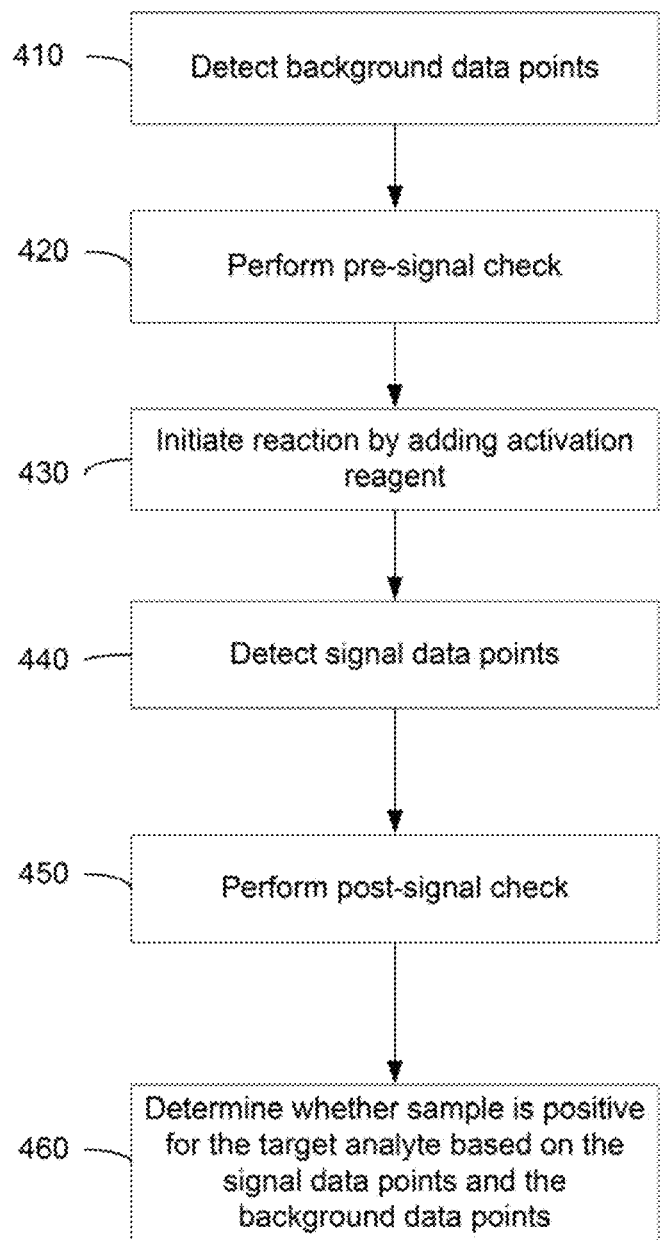
FIG. 4 is a flowchart of a method 400 for detecting a target analyte in a sample according to embodiments of the present invention.

FIG. 4 is a flowchart of a method 400 for detecting a target analyte in a sample according to embodiments of the present invention. Method 400 can be implemented using system 100. For example, portions of method 400 can be performed using a computer system.

At block 410, background data points are detected by a detector. The background data points can be detected after a sample is inserted, e.g., inserted into container 120. The background data can be transmitted from a detection instrument to a computer system for early analysis, e.g., as part of a pre-signal check.

At block 420, a pre-signal check is performed. The check is performed before any reaction is initiated and signal data points are collected. Thus, the check is called a "pre-signal" check. One or more pre-signal checks can be performed. Example pre-signal checks are described in more detail below. An example pre-signal check can determine whether structural aspects of the system exist, e.g., whether the detection instrument is not connected properly. In some embodiments, if the pre-signal check passes, then method 400 can proceed.

At block 430, a reaction is initiated by adding an activation agent to the sample. The reaction can cause a signal to be emitted, e.g., a light signal. The reaction may be as described above for the example of detecting MRSA.

At block 440, signal data points are detected by the detector. The signal data points can have a peak in a flash region, e.g., when the signal is positive for the analyte. The signal data points can be analyzed to determine whether the analyte is present in the sample.

At block 450, a post-signal check is performed. The check is performed after the signal data points are collected. Thus, the check is called a "post-signal" check. One or more post-signal checks can be performed. Example post-signal checks are described in more detail below. An example post-signal check can determine whether the signal data points show an aberration, and thus is indicative of an error. Another example post-signal check can use tailored criteria to identify low, positive signals. In some embodiments, if the post-signal check passes, then method 400 can proceed.

At block 460, it is determined whether the sample is positive for the target analyte based on the signal data points and the background data points. As an example, a signal-to-background term can be determined. A regression (e.g., at least a second order polynomial) can be performed, and accuracy term for the quality of the regression fit can be used to discount signals that are poor regression fits.

The determination is an example of a classification of the sample. For example, embodiments can use the signal-to-background term and the accuracy term to determine a score that is compared to a threshold to determine a classification. Examples of classifications include presence or absence of the analyte, indeterminate, or levels of confidence of the presence or absence.

III. Classification

Embodiments can optimize the classification process for determining whether a sample is positive for a target analyte in a flash reaction. The optimization can be performed to provide optimal sensitivity and specificity. For example, one or more parameters of a score can be selected to optimize a total for sensitivity and specificity, potentially to satisfy a requirement that the sensitivity and specificity are equal to greater than 95%.

Typically, in discriminant analysis, a linear combination of indirect measurements (Y) is derived, which separates the classes of direct measurements (X) in a way that future observation on indirect measurement could be classified on the basis of average distance between classes. In contrast, embodiments can derive a score and a threshold that maximize the separation between upper 95$^{th}$ percentile of Y data for one class of X versus the lower 95$^{th}$ percentile of Y data for another class. This approach can be extended to cases, where X corresponds to multiple classes and Y could be univariate or multivariate. In some embodiments, no assumption is made about the theoretical probability distribution of Y.

Different statistics were considered for separating (discriminating) between the upper 95$^{th}$ percentile of MSSA samples and the lower 95$^{th}$ percentile of MRSA samples so as to provide 95% specificity and 95% sensitivity, respectively. The statistics could be univariate or multivariate for this classification. Example statistics are: (1) Intercept and slope utilizing partial sample of substrate data (e.g., for different periods from 10 to 19.75 seconds); (2) Intercept and slope utilizing the partial sample of substrate and baseline data (for different periods from 10 to 19.75 seconds and from 5 to 9.75 seconds); (3) Sum of partial sample of substrate data/Sum of baseline data; and (4) Sum of partial sample of substrate data/Maximum of baseline data. For (1), based upon linear regression of data points from 10 to 19.75 seconds, intercept and slope could be determined for each sample. These intercept and slope could then be analyzed for percentiles for the two classes. Same applies to (2). A univariate statistic is defined below.

As part of determining the univariate statistic, first data on indirect and direct measurements is obtained for various samples. Multivariate data on the indirect measurements was simplified into one statistic. For example, embodiments can distill N of the collected data points into one metric that separates the two classifications (clusters). In examples below, the one metric (score) can separate the indirect measurements into two classes in such a way that the upper 95$^{th}$ percentile of MSSA is below the lower 95$^{th}$ percentile of MRSA. Accordingly, embodiments can provide that the classification system achieves a goal of specified sensitivity and specificity.

A. Use of Signal-to-Background and Curvature

In order to determine if a sample contains a target analyte (e.g., MRSA), embodiments can compute a score (S) and compare the value of this score to a classification threshold (T). If the score is greater than or equal to the threshold, the sample is deemed to be positive for the target analyte while if the score if less than the threshold, the sample is determined to be negative for the target analyte. The score and threshold can also be defined to have the opposite relationship for what is determined to be negative and positive.

In some embodiments, the score is calculated via the formula: $S = Rsn - Cxs \geq T$. The Rsn term is a signal-to-background term. The Cxs term is an accuracy term that is a measure of an accuracy of a fit of a regression function to the signal data points. Rsn can be calculated by the formula:

$$Rsn = \frac{Y - BM}{BS},$$

where Y is a sum of the signal data points (Sn), e.g., the data points between PKst and PKend where PKst=43 and PKend=59. Thus, Y can be defined as following: $Y = \Sigma_{n=PKst}^{PKend} Sn$. The Y term effectively integrates around the peak.

BM can be defined as BM=PS*Bm. Thus, BM is the product of the mean (or median, mode or sum of different terms) of the background data points, Bm, and the total data-points that encompass the signal data points, e.g., PS=17. BS is the product of the standard deviation (or range or quartile) of the background data points, Bs, and a constant W: BS=W*Bs. Cxs is the product of the parabolic coefficient of the quadratic least squared regression ($X^2$) and the coefficient of determination $R^2$ (or any measurement of accuracy) of the quadratic least squared regression: $Cxs = R^2 * X^2$. For a concave-down function, like the flash region, $X^2$ is negative. Thus, a good concave fit will increase the value of S, since the Cxs term is subtracted from Rsn. In embodiments where the accuracy term includes the parabolic coefficient, the parabolic coefficient can act as a weighting factor for how much the accuracy value decreases the score.

The accuracy measurement (e.g., $R^2$) becomes smaller when there is a bad regression fit, i.e., when the kinetics of the signal is not predominantly quadratic. A positive signal is predominantly quadratic, and thus a good fit will increase the score. The value of $X^2$ would be negative for a concave-down signal (i.e. parabola open down), as is present in FIG. 3. If a different weighting factor other than $X^2$ is used (e.g., just 1), then the accuracy term can be added to the signal-to-background term. Equivalently, the weighting factor can be −1, so that S=Rsn−Cxs can still be used.

The constants W and T can be chosen by calculating the S using a representative set of data from samples known to be positive and negative for the target analyte (e.g., MRSA) in order to achieve a specified sensitivity and specificity, e.g., sensitivity of ≥90% and specificity of ≥95%. In order to optimize the algorithm for data near the cut-off, i.e. for samples containing lowest amounts of the target analyte, the upper 95$^{th}$ percentile of the data known to be negative for the target analyte and the lower 95$^{th}$ percentile of the data known to be positive for the target analyte can be used.

The data can then be analyzed based on the following criteria:

True Positive (TP): A known MRSA positive sample that produces S≥T;

True Negative (TN): A known MRSA negative sample that produces S<T;

False Positive (FP): A known MRSA negative sample that produces S≥T; and

False Negative (FN): A known MRSA positive sample that produces S<T.

The sensitivity and specificity can be calculated using the representative set of data from the known samples and the following formulas: Sensitivity=TP/(TP+FN) and Specificity=TN/(TN+FP). In this manner, the constants W and T can be chosen such that the algorithm achieves the desired sensitivity and specificity. In one implementation, the desired sensitivity is ≥90% and desired specificity is ≥95%.

Figure 5:
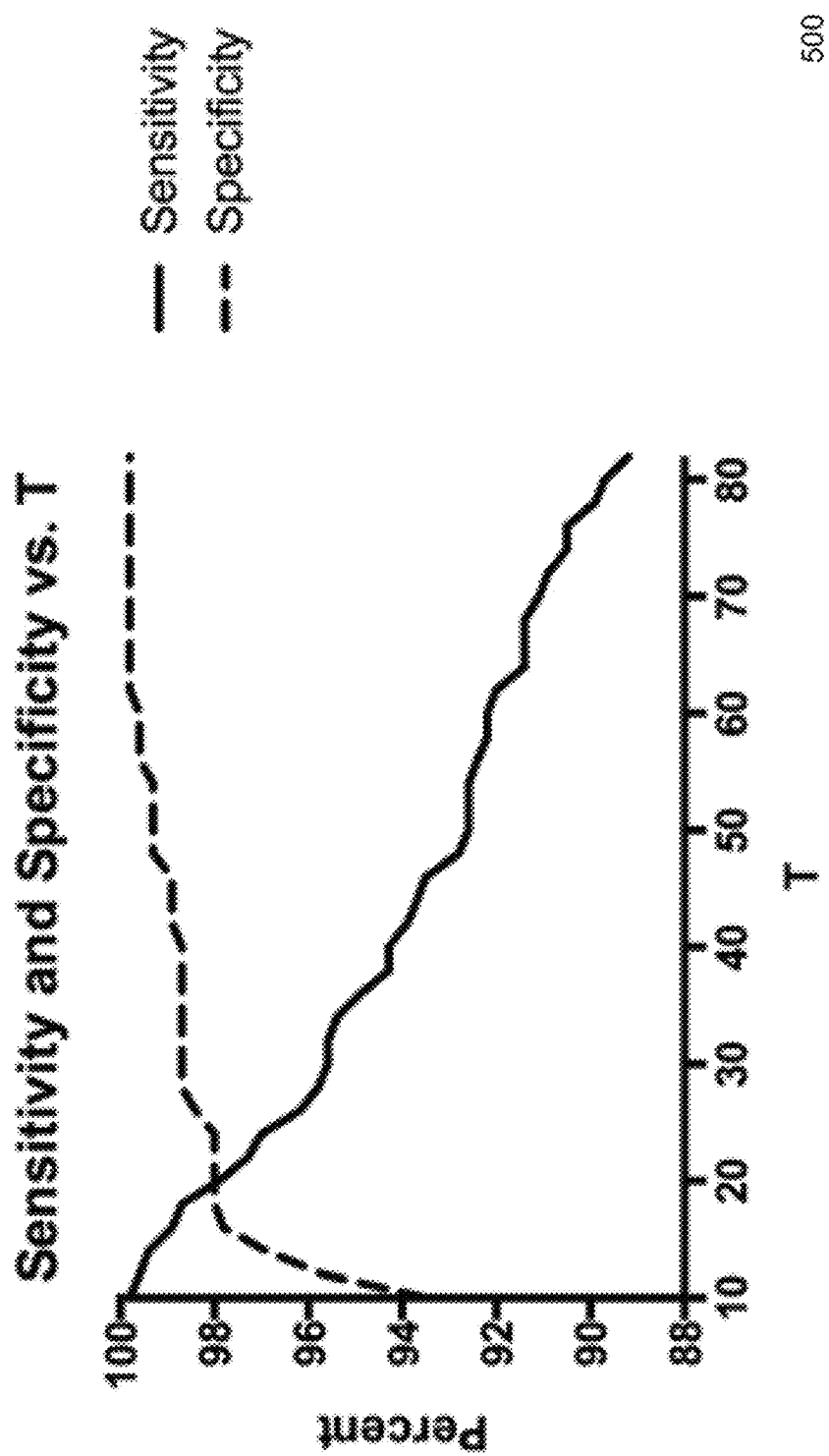
FIG. 5 depicts an example of values of Sensitivity and Specificity vs. threshold (T) values according to embodiments of the present invention.

FIG. 5 depicts an example of values of Sensitivity and Specificity vs. threshold (T) values when parameter W has a value of 15 according to embodiments of the present invention. Based on this data analysis, a value of 18 is chosen for T to optimize the sensitivity and specificity. Another example value of T is 12.

B. Example

As an example, the score can be determined as follows:

$$\frac{\text{Sum }(10.75 \text{ to } 14.75) - [\text{average}(5.25 \text{ to } 9.50)*17]}{\text{StDev}(5.25 \text{ to } 9.50)*15} -$$

$$X^2 \text{Coefficient (parabolic fit }(10.75 \text{ to } 14.75)*R^2 \geq 12$$

The sum is for the signal data points between time of 10.75 and 14.75. The average is for the background data between 5.25 to 9.50. StDev is the standard deviation of the background data between 5.25 to 9.50.

The parabolic fit means a $2^{nd}$ order least-squares regression is to be generated on nine data points between 10.75 and 14.75. The $X^2$ coefficient corresponds the $2^{nd}$ order coefficient of the least-squares regression curve. The parabolic fit data point #5 is at the local maximum (10.75-14.75), effectively centering the parabola on the local maximum, with four data points (one second in time) on either side. In some embodiments, if there are multiple points having the same value (e.g., two neighboring points having a same local maximum value), the one closest to the injection peak can be chosen.

If the local maximum (10.75-14.75) is between 10.75 and 11.5, the parabolic fit will be centered around 11.75. If the local maximum (10.75-14.75) is between 14.0 and 14.75, the parabolic fit will be centered around 13.75.

Accordingly, in some embodiments, the classification of the presence of a target analyte can use both a signal-to-background term and parabolic fitting methods. To compute the signal-to-background term($R_{sn}$), a sum (Y) of the signal data can be computed using two configurable parameters of: $P_{is}$—number of data points spanning an injection spike (e.g., set to 3); and $P_{ss}$—number of data points that make up the specified range (set to 17). The signal data is $P_{ss}$ data points of the detected substrate data points starting at $P_{is}$ data points after the start of the first substrate data point. The mean (BM) of the background data points excluding the first and last data points is calculated and multiplied by $P_{ss}$. The standard deviation (Bs) of the baseline read excluding the first and last data points is multiplied by a parameter W, e.g., a fixed constant of 15. A signal-to-background term can be computed as $R_{sn}=(Y-BM)/(W*Bs)$.

An accuracy term $C_{xs}$ of the signal data to a parabolic fit can be computed as follows. The maximum data point (M) of the signal data is found. A parabolic fit can be computed using a $2^{nd}$ order least squares regression on nine (9) data points of the signal data, using four data points on either side of M If the time point of M is 3 data points or less from the start of the signal data, then the parabolic fit can be centered on the time point of 4 data points after the start of the signal data. If the time point of M is within 3 data points from the end of the signal data, then the parabolic fit can be centered on the time point of 4 data points from the end of the signal data. $C_{xs}$ can be computed by multiplying the coefficient of the $X^2$ term from the parabolic fit with an accuracy value, e.g., a coefficient of determination value $R^2$ (r-squared). Other examples of an accuracy value are adjusted r-squared, p-value of F-test, and predicted residual error sum of squares (PRESS) statistic.

A raw score S can be computed as $S=R_{sn}-C_{xs}$. A configurable parameter of a threshold T (e.g., 12) can be used for determining if sample is positive/negative. If $S \geq T$, then the sample is positive (MRSA), else the sample is negative (not MRSA).

C. Method

Figure 6:
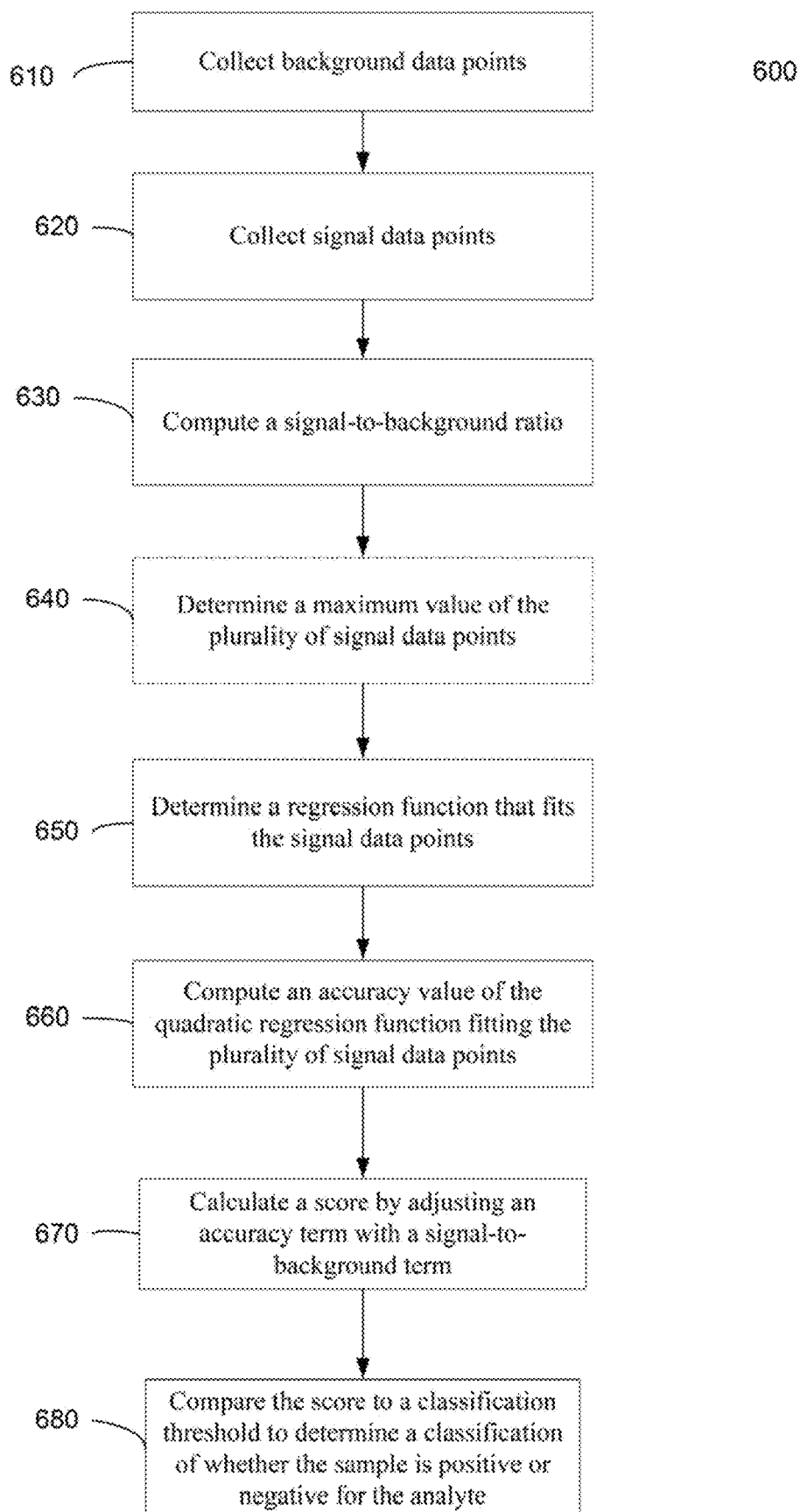
FIG. 6 is a flowchart of a method for determining whether a sample is positive for an analyte according to embodiments of the present invention.

FIG. 6 is a flowchart of a method 600 for determining whether a sample is positive for an analyte according to embodiments of the present invention. Method 600 can be performed at least partially by a computer system.

At block 610, a plurality of background data points is collected using a detector. As an example, the detector can be a light detector (e.g., a PMT). Other examples of detectors include pH or ion/charge-based detectors. The background data points are collected during a background time interval. The background time interval can occur prior to receiving a signal, e.g., as shown in FIG. 3 with region B.

At block 620, a plurality of signal data points is collected using the detector. The plurality of signal data points is collected during a signal time interval, which may be after the background time interval. The signal time interval includes a portion of time after a sample is activated by an activation reagent. For example, the signal time interval can correspond to the Sn region of FIG. 3.

At block 630, a computer system can compute a signal-to-background ratio using the plurality of background data points and the plurality of signal data points. In one embodiment, the signal-to-background ratio is computed as a ratio of an area under the signal curve less the mean of the background, and the result is divided by a standard deviation of the background, e.g., the signal-to-background ratio can be computed as $$\frac{Y - BM}{BS}$$

where Bs is the standard deviation of the background. Further examples of signal-to-background ratios are described in section III. For example, a signal-to-background ratio Rsn can be determined as $$Rsn = \frac{Y - BM}{BS} = \frac{Y - BM}{W*Bs}.$$

Other statistical values besides a mean can be used for BM, e.g., a median, mode, or sum of different terms. Other measures of deviation can be used for BS besides the stand deviation. For example, a specific range of values, percentages of values, ranks of values, or quartiles of values. In another example, the BM term can be excluded, which would result in a different classification threshold.

At block 640, the computer system optionally can determine a maximum value of the plurality of signal data points. The maximum value can correspond to a peak of a signal curve. For example, FIG. 3 shows a peak in flash region 310. If two signal data points are equal in being the highest, some embodiment can use either one as the maximum value. In a further embodiment, the peak can be taken as being between two such signal data points.

At block 650, computer system determines a regression function that fits the plurality of signal data points. The regression function includes at least a second order polynomial. The regression can be determined using a time of the maximum value, e.g., for centering the regression function. The regression can use least squares as the metric for determining a best fit for the three parameters of the regression function.

The plurality of signal data points used in determining the regression can be defined to be in a specific interval, i.e., not all signal data points may be used. For example, a maximum value of the signal data can be determined and used to conduct a regression of the data using data points (e.g., 4) before the maximum and data points (e.g., 4) after the maximum. Thus, points adjacent to the maximum can be used. In the embodiment where four data points are used on either side of the maximum, if the maximum lies three data points or less from the start of the signal data, then the parabolic fit can be centered on the time point of the 4th data point after the start of the signal data. If the maximum lies three data points or less from the end of the signal data, then the parabolic fit can be centered on the time point of 4th data point before the end of the signal data. In one implementation, if two or more data-points have the same maximum value, then the first one is used.

In some implementations, if the maximum value of the signal is less than a predetermined amount, then the center of the regression can be set to a minimum predetermined amount. In other implementations, if the maximum value of the signal is greater than a predetermined amount, then the center of the regression can be set to a maximum predetermined amount.

At block 660, the computer system can compute an accuracy value of the regression function fitting the plurality of signal data points. In some embodiments, the accuracy value is the coefficient of determination $R^2$. Other embodiments can use a sum of the squares of the differences between the signal data points and the regression function, where the sum of the squares can be normalized, e.g., by the number of data points, the variance in the data, and the like.

At block 670, the computer system calculates a score by adjusting an accuracy term with a signal-to-background term. The adjusting can be done by subtraction or addition. The accuracy term includes the accuracy value. For example, the accuracy term can include a parabolic coefficient of a second order term of the regression function. Specifically, the accuracy term can include the accuracy value multiplied by the parabolic coefficient, as described above for Cxs. The signal-to-background term includes the signal-to-background ratio. For example, the signal-to-background term can be computed by multiplying the signal-to-background ratio by a reciprocal of a first constant.

At block 680, the score is compared to a classification threshold to determine a classification of whether the sample is positive or negative for the analyte. The classification threshold (e.g., T as referred to above) can discriminate between positive and negative samples. The value of T can be selected to optimize the achieved sensitivity and specificity, e.g., as shown in FIG. 5.

More than one classification threshold can be used. In such an embodiment, the classifications can include other classifications besides positive or negative, such as different levels of confidence for positive or negative. Indeterminate is an example of a classification.

D. Signal-to-Background Term

As part of determining the signal-to-background term Sn, a longitudinal analysis can be performed by integrating over multiple data points occurring over time, e.g., data points detected every ¼ seconds for a new data point. This longitudinal analysis can correspond to a signal part, where sustained values can be favored over a high peak that rises and falls fast. The average background can be used to account for an elevated signal that is specific to a given measurement (e.g., different detectors can have different gains). A deviation term in the denominator can account for noise (e.g., one system can have more noise than another).

The signal-to-background term can also include scaling factors. For example, the signal-to-background ratio can be multiplied by 1/W, where W is a constant (e.g., 15). The value for the parameter W can be determined by optimizing the achieved sensitivity and specificity. In some embodiments, two parameters W and T can be determined in this manner. A three-dimensional plot can be determined for W and T being dimensions, and the third dimension being the plots of the percent for the sensitivity and the specificity. Thus, as is done in FIG. 5 for a fixed value of W, optimal values for W and T can both be determined simultaneously.

In various embodiments, the signal Sn (e.g., 17 points following the injection peak) could be a region smaller or greater than 17, as long as it spans the flash portion of the signal. This region is integrated as the Y term described above. With a Sn few points, it can be important to center the integration on the peak as described above. Likewise, the mean background (the BM term from above) could be a region larger or smaller than examples above, and used to provide both the mean background and the standard deviation (the BS term from above). A smaller region would sacrifice some precision for a faster measurement, and correspondingly a larger region could provide some increased precision for a slower measurement.

E. Accuracy Term

The accuracy term can measure the peak dynamics of the signal data points, that is, whether the peak has characteristics of a flash reaction. Specifically, the accuracy term relates the peak dynamics to a quadratic or other regression function so as to help in the discrimination between positive and negative samples. If the peak of the signal resembles the chosen regression function then it is more likely the sample is positive, as the regression function is chosen to resemble positive signals. The accuracy value measures how closely the signal data points (or a portion of the signal data points) resemble the regression function.

In some implementations, the accuracy term is the product of the quadratic coefficient resulting from a regression (named $X^2$ above) with coefficient of determination $R^2$. There are alternatives for these two metrics in the accuracy term. For example, the $X^2$ term could be derived from a higher order polynomial fit of data (e.g., 4th or 5th order). In addition, the region of data analyzed in the regression could be smaller or larger than example regions provided above. Similarly for the term $R^2$, alternative measures of accuracy can be used, e.g., the so-called adjusted $R^2$ and predictive $R^2$.

In embodiments where the accuracy term includes the parabolic coefficient, the parabolic coefficient can act as a weighting factor for how much the accuracy value decreases the score. A positive signal would normally be concave-down, which has a negative value for the parabolic coefficient. Thus, the accuracy term would typically be negative and increase the score when the accuracy term is adjusted with the signal-to-background term. Any suitable weighting factor can be used, e.g., just −1. If the parabolic coefficient is positive, then this reduces the score, as it even more unlikely that a positive signal would be convex-up.

IV. Pre-Signal Check

These checks are applied before the injection of the substrate, which is the beginning of the flash reaction.

A. Identifying Aberrant Background Data

Erratic data may be a result of a malfunctioning PMT that may produce unreliable data. In a well-functioning PMT, the noise in the system is expected to exhibit Poisson statistics and the standard deviation of the noise is the expected to be equal to the square root of the mean of the noise. Based on this insight, embodiments can check if un-expected data is collected from the background. Other statistical distributions may be used besides a Poisson distribution, e.g., for different types of detectors.

Accordingly, the background data points before injection can be analyzed, e.g., the background data points in region B of FIG. 3. A median value is determined. The median and mean should be same for distribution. For a Poisson distribution, the variance the same is the same as the mean. The data points of the background should follow the Poisson distribution. Thus, if the median shows different characteristics than the mean, then the background can be identified as aberrant, e.g., due to improper installation of the sample container with the detector.

As part of the check, the median can be considered to be the mean. The median is not sensitive to outliers. The median is used to determine a standard deviation STD of the background data points. The number of data points greater than 2*STD plus the median are counted. If the number of data points is greater than a threshold (e.g., 5), then the background is too noisy and the sample container needs to be re-installed. The high noise is an indication of artifacts in the signal causing readings to be elevated.

In one example implementation, the median of the background is subtracted from each data point of the background and the remainder is compared to the product of the square root of the median of the background and a first constant. The median is used instead of the mean for this calculation in order to be insensitive to data point outliers which would be present in an aberrant signal. The median and mean have the same statistical value for non-aberrant data. The number of data points for which the left hand side of the formula yields a number that is greater than the right hand side of the equation are enumerated. If this sum is greater than a second constant, it is determined that the background is producing un-expected data, and the system is deemed unsuited for further data analysis. In such a situation, the sample container can be re-seated with the PMT. If this sum is less than or equal to the second constant, it is determined that the background is not producing un-expected data and the system is deemed suitable for further data analysis. The first and second constant may be determined empirically and were chosen to be 2 and 5, respectively.

Accordingly, some embodiments can calculate a median of at least a portion of the background data points, and then calculate a deviation using the median. For example, the deviation can be the square root of the median, which would correspond to the standard deviation for a Poisson distribution. A first cutoff can be determined using a sum of the median and the deviation. This first cutoff would be equivalent to subtracting the median and then comparing the resultant data points to a deviation term (e.g., 2 times the deviation). Two is an example of the first constant mentioned above. A first number of background data points that are greater than the first cutoff can be counted and compared to a second cutoff (e.g., 5 as referred to for the second constant above). When the first number is greater than the second cutoff, it is determined that an error exists. This error can be the result of problems with the system (e.g., the detector). An alert can be sent to a user as an indication of the error.

When the test is done prior to collecting the plurality of signal data points, the system can be re-connected so that the sample is not wasted. This pre-signal check can be performed again to ensure that the error does not still exist. Thus, in one embodiment, the plurality of signal data points are not collected until the error is corrected as determined by the first number being less than or equal to the second cutoff. In other embodiments, repositioning can be made up to a specified number of times (e.g., 3) and then if not resolved, a method can proceed.

B. Mean is Greater than a Threshold

An elevated background signal may be a result of a malfunctioning PMT that may produce un-reliable data, or it may be due to other factors including aberrant light from external sources, premature activation of signal in the assay, which may result in unreliable results. Embodiments can check if an elevated background is observed. The mean of the background can be compared to a pre-determined factor (e.g., 40)

If the mean of the background is greater than the predetermined factor, it is determined that the background is elevated, and the system is deemed unsuited for further data analysis. In such a situation, the sample container can be re-seated with the PMT. If the mean of the background is less than or equal to the predetermined factor, it is determined that the background is not elevated, and the system is deemed suitable for further data analysis.

The predetermined factor may be chosen from an analysis of the detector noise. A prior period (e.g., region N from FIG. 3) of data collection may be obtained, prior to exposing the detector to the sample. In this prior period, a shutter mechanism can block light from the detector sensor. Statistics of this 'dark' data may be used to dynamically choose the predetermined factor. For example, the predetermined factor may be calculated as the mean of the dark data or as a product of the mean of the dark data and a constant.

V. Post-Signal Check

The following checks are applied after the signal data is collected. The post-signal checks can be done before or after a score is used to determine a classification regarding the analyte (e.g., via method 600).

A. Screening Using Dynamic Threshold

The sensitivity and specificity can be further increased for signals that have small peaks. A separate threshold analysis can be performed; and if the signal passes this initial threshold, then method 600 can be performed in another threshold test. Since the signal produced by the target analyte exhibits particular kinetic characteristics, a non-specific signal, not produced from the target analyte, may be distinguished from specific signal that is produced by the target analyte based on analysis of the kinetic characteristics of the signal.

In some embodiments, a dynamic (adaptive) threshold is used as peaks could be quite small. This initial threshold test is used to determine whether to proceed. This initial threshold can be based on the magnitude of the signal. If the peak magnitude is below a fixed threshold, then an adaptive threshold can be used. If the signal passes this test, then the above scoring can be performed. But, it if it fails, then the signal is identified as negative.

As the peaks are smaller, the Poisson fluctuations in the data points have more impact. Thus, an actual positive signal that is small would look noisy. Based on where the maximum is (between certain levels), then an amount of expected noise for a small positive signal is determined. The amount of noise for the small positive signal is determined based on known positive signals.

For a given peak value, the amount of expected noise is determined, e.g., using Monte Carlo techniques based on expected levels of noise seen in real signals. For example, a real signal can be identified and the signal value decreased. Monte Carlo is implemented for the level of noise expected for each peak value based on Poisson statistics. The Monte Carlo technique can use a single noiseless characteristic assay signal. This single noiseless signal can be mathematically scaled to different signal levels, including expected low level signals. At each scaled level, the amount of expected noise is determined using the Monte Carlo technique. This determination can be done for a range of scaled signal levels to characterize the expected noise at various signal levels.

Based on the simulations of noise, an expected accuracy (e.g., $R^2$) of a functional fit (e.g., a $4^{th}$ order fit) can be determined. This is done for multiple peak values, and an interpolation is performed between them. The interpolation can be on a logarithmic scale (e.g., 2), so there are finer gradations as the peaks get smaller. Thus, for any peak value, an accuracy threshold can be determined based on the maximum value. If the accuracy value for a current signal is above the threshold, then the signal passes, and embodiments can proceed to the scoring threshold (e.g., block 460).

In one example, embodiments can check the following. If the standard error of the linear regression of the Sn region is above a threshold (i.e. a strong signal), the signal profile is expected to be smooth and cannot exhibit a concave up profile. If the signal is below a threshold (i.e. a weak signal), the peak profile is expected to be 'noisy' and can be modeled by a $4^{th}$ order polynomial convoluted with noise of Poisson distribution or other statistical distribution, e.g., if a detector other than a PMT is used. If the signal does not exhibit these characteristics, then it is flagged as not specific signal, and a scoring method described above does not process the data.

In one implementation, data-points in the Sn signal region (e.g., ranging from 43-59) are analyzed. The data is first filtered by calculating a median value of every three adjacent data points starting offset by 1 from the beginning and ending 1 before the end of the Sn region, thus skipping the endpoints, which are treated differently. The resulting median value replaces the middle of the 3 data points.

The rightmost data point is replaced with the median of the last two data points; since this is on the tail, this is a good approximation. The leftmost data point is adjacent to the injection peak, the P is region. To filter this leftmost point, it is tested for being an outlier (e.g., greater than the value of the left-most point calculated from a $4^{th}$ order polynomial fit of the filtered data plus a specified number (e.g., 3) times its standard deviation). If the leftmost point is an outlier, an extrapolated value (the value of the left-most point calculated from a $4^{th}$ order polynomial fit of the filtered data) is substituted. A $4^{th}$ order polynomial fit of the filtered data including the processed end points is then performed and the R-squared value of the fit is calculated.

The peak value is determined as the maximum value in the Sn signal region (e.g., ranging from 43-59). If the peak value is above a large peak threshold (e.g., 810 RLU) and the R-squared of the fit is less than a threshold (e.g., 0.97), then the data is flagged as aberrant. If the R-squared of the fit (or other accuracy metric) is above the threshold, then the process can proceed to determining a score.

If the peak value is below a low peak threshold (chosen to be 200 RLU), then an adaptive accuracy threshold (e.g., an R-squared threshold) can be computed. Otherwise, a constant R-squared threshold (e.g., 0.93048) can be used. The adaptive threshold can be computed as a linear combination of various powers of the peak height (maximum value), where the power may be of a log of the peak height. Coefficients of the linear combination can be determined by fitting the accuracy measures (e.g., $R^2$) determined at different peaks. For example, the adaptive R-squared threshold can be computed using the formula: $\Sigma_{i=0}^{2}[Bi*(\log(peak))^i]$, where peak is the peak value.

As an example, B0=−0.69650, B1=1.37009, and B2=−0.28814 can be determined empirically in the following manner. The values of the B constants in the formula are determined by performing a $4^{th}$ order polynomial fit of data determined to be positive for the analyte and exhibiting a peak below the low peak threshold. A Monte-Carlo simulation is then conducted on the fit data convoluted with 10,000 iterations of noise exhibiting Poisson distribution. In one implementation, each individual value from the single-scaled noiseless signal is a mean value. This mean value is used to create a single Poisson distributed value (a noisy value) for that point in the signal. This is done for each point in the signal to simulate one signal needed for each iteration of the 10,000 Monte Carlo iterations.

Simulations are conducted for simulated data consisting of the fit data adjusted for varying peak values below the low peak threshold. The average and standard deviation of the R-squared from the simulations is computed for each peak value. A mathematical relationship is then established between these low peak values and the mean R-squared minus 3 standard deviations of the R-squared (the adaptive threshold). The constants B0, B1 and B2 represent this mathematical relationship, which is the adaptive R-squared threshold for low peaks.

The signal data is flagged as aberrant (i.e. negative) if the R-squared of the data is less than the R-squared adaptive threshold. The signal data can also be flagged as aberrant if the quadratic parameter of the $4^{th}$ order polynomial fit of the data is positive, and if the standard error of the data is less than predetermined value (e.g., 25). For this test, the R-squared threshold is either the adaptive R-squared threshold for peaks less than 200 RLU or the constant R-squared threshold of 0.93048 for larger peaks, which are less than the large peak threshold.

Accordingly, a high-order regression function can be determined using the plurality of signal data points, with the high-order regression function being a $4^{th}$ order polynomial or higher. Some or all of the signal data points may be used. An accuracy measure of the high-order regression function is computed, e.g., an $R^2$ value. The maximum value of the plurality of signal data points can be compared to one or more initial thresholds (e.g., the large and low peak thresholds above). An accuracy threshold is selected based on the comparison to the one or more initial thresholds. For example, as described above, different $R^2$ thresholds can be used for different peak values, including using an empirical function or constants for different initial thresholds. The accuracy measure is compared to the accuracy threshold to determine whether the sample is negative for the analyte based on the accuracy measure being less than the accuracy threshold. If the accuracy measure is greater than or equal to the accuracy threshold, then embodiments can proceed to determining a score and comparing it to a classification threshold, e.g., as described for FIG. 6.

B. Linearity Check

A signal may be flagged as aberrant if it exhibits a linear and flat profile. Embodiments can perform a linear regression of the data-points in an extended Sn region ranging from 43-79. If the lower and upper bounds of the confidence interval (e.g., 10%) of the slope of the linear regression include the value zero, then the data is flagged as aberrant. Thus, if the signal has a slope close to zero, then the data can be flagged as aberrant, e.g., no peak.

VI. Results

A. Sensitivity and Specificity 182 nasal swab samples from anonymous hospital patient donors were collected and processed via the MRSA non-replicative transduction particle assay as described in WO 2014/160418 using the system described in WO 2014/164768 and cartridges described in PCT/US15/27519. In the assay, data is produced as RLU values vs. time, e.g., as depicted in FIG. 3. The data was then analyzed using a scoring algorithm (labeled S/B-quad) of an embodiment of the present invention as well as via an analysis of maximum RLU.

For the maximum RLU analysis, cutoff values were produced by analyzing the maximum RLU from 120 negative control samples consisting of samples containing *S. epidermidis* and no MRSA in the samples. The cutoff values consisted of the average maximum RLU of the negative control samples, the average plus one-times the standard deviation of the maximum RLU of the negative control samples, the average plus two-times the standard deviation, and the average plus three-times the standard deviation. In order to determine if a clinical sample is positive for MRSA, the maximum RLU from the clinical sample is compared to the cutoff values. If the maximum RLU of the clinical sample is less than the cutoff, then the sample is considered negative for MRSA, otherwise if the maximum RLU is greater than or equal to the cutoff value, the sample is considered positive for MRSA.

The results from this analysis are summarized in FIG. 7. The analysis does not include pre-signal or post-signal checks. Thus, the results show improvements attributable to method 600.

The sensitivity, specificity, positive predictive value, negative predictive value, and percent agreement including the lower and upper bound of the 95% confidence interval for each metric were calculated by comparing the MRSA positive/negative results for each analysis vs. the known MRSA results for each sample as determined via a reference enriched culture-based assay as described in '*FDA Draft Document—Establishing the Performance Characteristics of Nucleic Acid-Based In vitro Diagnostic Devices for the Detection and Differentiation of Methicillin-Resistant Staphylococcus aureus* (*MRSA*) and *Staphylococcus aureus* (*SA*); Issued on Jan. 5, 2011'.

As can be seen from the results, the scoring analysis (S/B-quad) produced superior results to that of analysis conducted based on maximum RLU, where the scoring results produced values of greater than 90% for all performance metrics.

The superior performance of embodiments of the scoring algorithm is attributed to the fact that the algorithm takes into account the shape of the RLU vs. time results whereas a maximum RLU analysis does not. As a consequence of this, a maximum RLU analysis is prone to producing discordant results.

B. High Background Signal

Figure 8A:
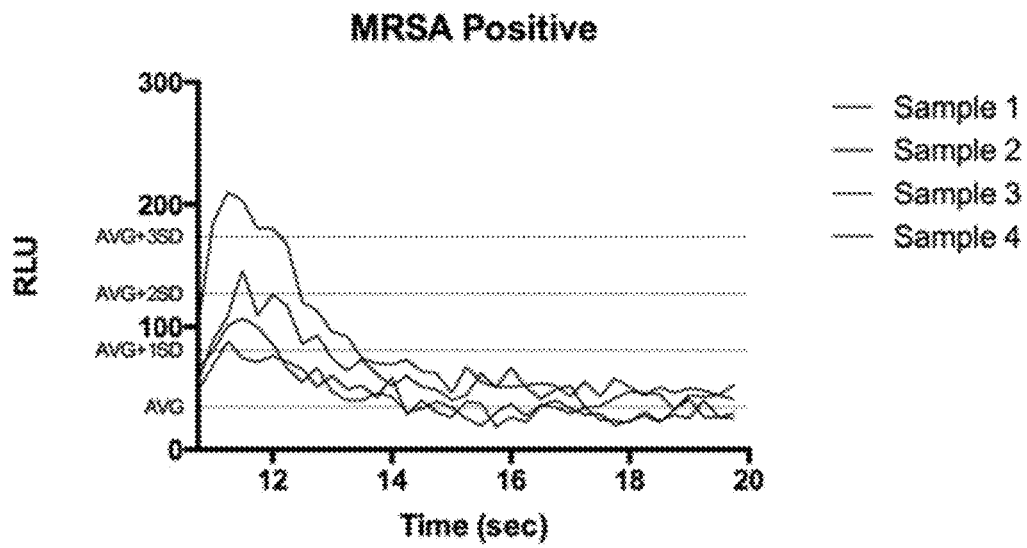
FIGS. 8A and 8B shows graphs comparing accuracy results of classifications using a maximum signal and accuracy results using scores according to embodiments of the present invention.
Figure 8B:
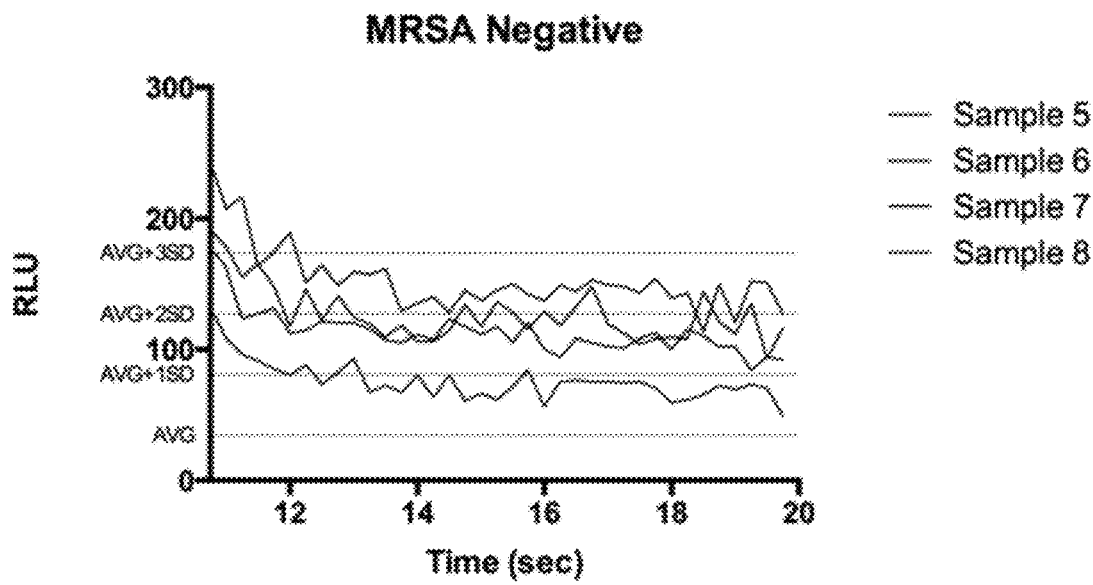

FIGS. 8A and 8B shows graphs comparing accuracy results of classifications using a maximum signal and accuracy results using scores according to embodiments of the present invention.

The data in FIGS. 8A and 8B highlights the superiority of the scoring algorithm when compared to an analysis based on maximum RLU, in particular when the system exhibits signals of non-specific light (e.g., high background signal). The plots show RLU vs. time data from 8 clinical samples tested for the presence of MRSA. The horizontal dotted lines show the RLU threshold values based on the Average Maximum RLU of MRSA negative control samples as well as the Average Maximum RLU plus one, two, and three standard deviations of the Maximum RLU of MRSA negative control samples. Samples 1-4 were shown by a reference method to be positive for MRSA while samples 5-8 were shown by a reference method to be negative for MRSA. The scoring algorithm classified samples 1-4 as MRSA positive and samples 5-8 as MRSA negative demonstrating 100% concordance with the reference method. In the case that an Average Maximum RLU plus two standard deviations were used to determine the classification of a sample, samples 2, 4, 5, 6, 7, and 8 would have been classified as negative thus resulting in two False Negative results and four False Positive results.

VII. Computer System

Figure 9:
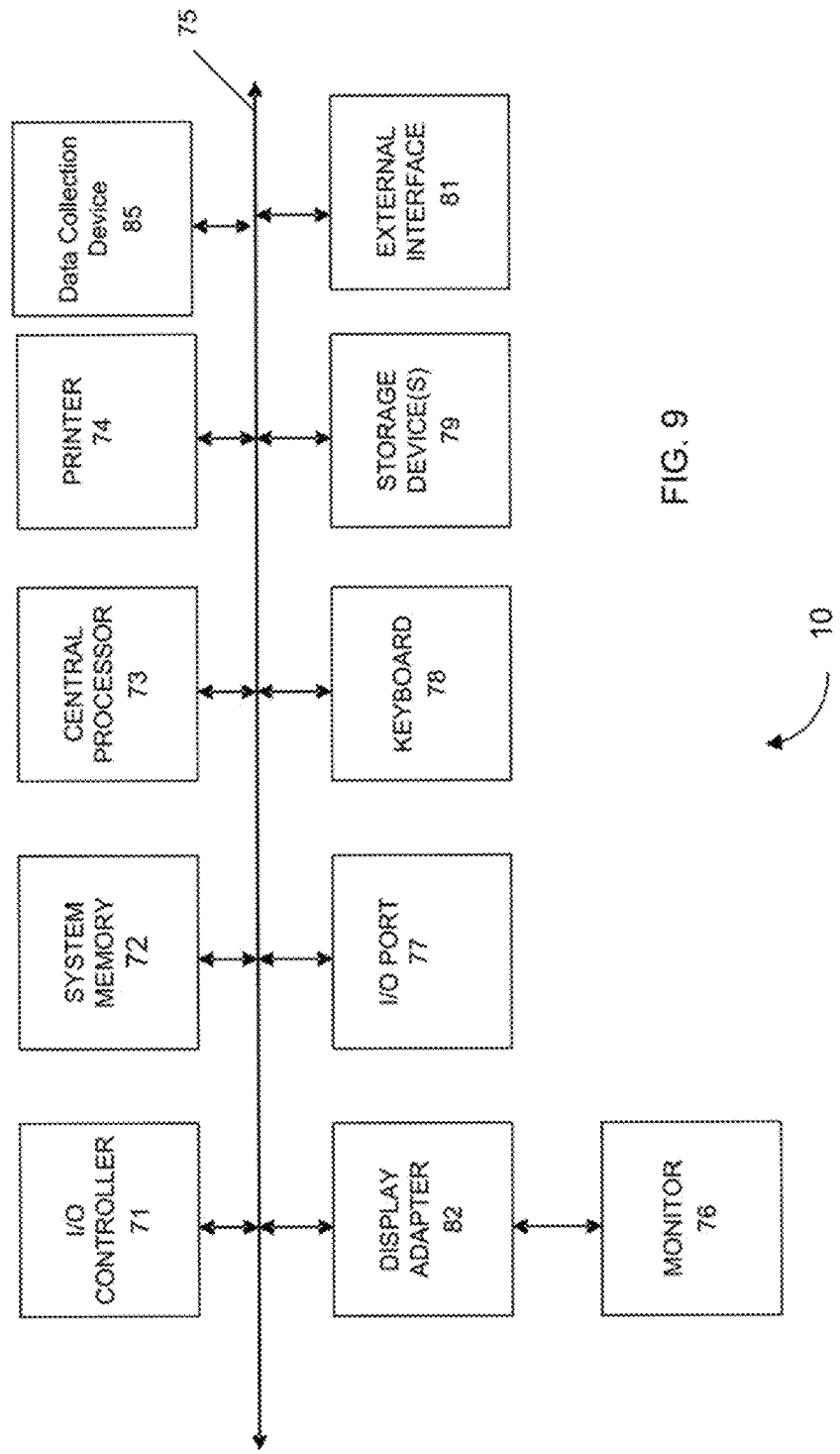
FIG. 9 shows a block diagram of an example computer system usable with system and methods according to embodiments of the present invention.

Any of the computer systems mentioned herein may utilize any suitable number of subsystems. Examples of such subsystems are shown in FIG. 9 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 9 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method for detecting an analyte in a sample, the method comprising:
   collecting a plurality of background data points using a detector, the background data points collected during a background time interval;
   initiating activation of the sample by an activation reagent;
   collecting a plurality of signal data points of a flash luminescence signal associated with the sample using the detector, wherein the plurality of signal data points is collected during a signal time interval that is after the background time interval, wherein the signal time interval includes a portion of time after the sample is activated by the activation reagent;
   computing, by a computer system, a signal-to-background ratio using the plurality of background data points and the plurality of signal data points;
   determining, by the computer system, a regression function that fits the plurality of signal data points, wherein the regression function includes at least a second order polynomial;
   computing, by the computer system, an accuracy value of the regression function fitting the plurality of signal data points;
   calculating, by the computer system, a score by adjusting an accuracy term using a signal-to-background term, the accuracy term including the accuracy value, and the signal-to-background term including the signal-to-background ratio; and
   comparing the score to a classification threshold to determine a classification of whether the sample is positive or negative for the analyte.

2. The method of claim 1, wherein:
   if the score is less than the classification threshold, the sample is determined to be negative for the analyte, and
   if the score is greater than or equal to the classification threshold, the sample is determined is determined to be positive for the analyte.

3. The method of claim 1, further comprising:
   computing a weighted sum of squared errors of the regression function relative to the plurality of signal data points; and
   calculating the accuracy term by multiplying the accuracy value by the weighted sum of squared errors.

4. The method of claim 1, wherein the accuracy value is selected from: include r-squared, adjusted r-squared, p-value of F-test, and predicted residual error sum of squares (PRESS) statistic.

5. The method of claim 1, wherein the regression function includes a parabolic coefficient of a second order term, and wherein the accuracy term includes the accuracy value multiplied by the parabolic coefficient.

6. The method of claim 1, further comprising:
computing the signal-to-background term by multiplying the signal-to-background ratio by a reciprocal of a first constant.

7. The method of claim 1, where the classification threshold is chosen to obtain a desired sensitivity and specificity with reference to representative sets of data having known results for presence of the analyte.

8. The method of claim 1, wherein the detector is a light detector, and wherein the plurality of signal data points form a luminescence signal.

9. The method of claim 1, wherein the analyte is methicillin-resistant *Staphylococcus aureus* (MRSA).

10. The method of claim 1, wherein the background time interval is prior to activation of the sample by the activation reagent, and wherein the plurality of background data points are collected from the sample before the activation of the sample.

11. The method of claim 1, further comprising:
calculating a median of at least a portion of the background data points;
calculating a deviation using the median;
determining a first cutoff using a sum of the median and the deviation;
counting a first number of background data points that are greater than the first cutoff;
comparing the first number to a second cutoff; and
when the first number is greater than the second cutoff, determining that an error exists.

12. The method of claim 11, further comprising:
repositioning the sample relative to the detector.

13. The method of claim 12, wherein the plurality of signal data points are not collected until the error is corrected as determined by the first number being less than or equal to the second cutoff.

14. The method of claim 1, further comprising:
calculating a mean of at least a portion of the background data points;
comparing the mean to a predetermined factor; and
when the mean is greater than the predetermined factor, determining that an error exists.

15. The method of claim 14, further comprising:
determining the predetermined factor using data points collected when a sensor of the detector is blocked.

16. The method of claim 11, wherein the plurality of signal data points are not collected until the error is corrected as determined by the first number being less than or equal to the second cutoff.

17. The method of claim 1, further comprising:
determining, by the computer system, a maximum value of the plurality of signal data points, wherein the regression function is determined using a time of the maximum value.

18. The method of claim 17, wherein the regression function is centered at the time of the maximum value.

19. The method of claim 17, further comprising:
determining a high-order regression function using the plurality of signal data points, the high-order regression function being a $4^{th}$ order polynomial or higher;
computing an accuracy measure of the high-order regression function;
comparing the maximum value of the plurality of signal data points to one or more initial thresholds;
selecting an accuracy threshold based on the comparison to the one or more initial thresholds; and
comparing the accuracy measure to the accuracy threshold to determine whether the sample is negative for the analyte based on the accuracy measure being less than the accuracy threshold.

20. The method of claim 19, further comprising:
determining that the sample is possibly positive for the analyte based on the accuracy measure being greater than the accuracy threshold; and
proceeding to use the comparison of the score to the classification threshold to determine the classification of whether the sample is positive or negative for the analyte.

21. The method of claim 19, further comprising:
filtering the plurality of signal data points to obtain a filtered dataset by applying a statistical smoothing function to the plurality of signal data points; and
using the filtered dataset to determine the high-order regression function.

22. The method of claim 21, wherein filtering the plurality of signal data points includes:
for each signal data point of at least a portion of the signal data points:
calculating a median value of adjacent data points and the signal data point; and
replacing the signal data point with the median value.

23. The method of claim 22, wherein each of the median values are determined from three signal data points.

24. The method of claim 23, wherein the portion of the signal data points is offset by one data point from a beginning signal data point and ending one data point before an ending signal data point of the signal time interval,
wherein the ending signal data point is replaced with a median of a last two signal data points,
wherein the beginning signal data point is replaced by a corresponding value from the high-order regression function if the beginning signal data point is greater than the corresponding value plus a specified number times a standard deviation, and
wherein the accuracy measure is of the high-order regression function fit to the filtered dataset.

25. The method of claim 19, wherein the one or more initial thresholds include a first initial threshold and a second initial threshold, wherein the accuracy threshold is a first constant when the maximum value is greater than the first initial threshold, and wherein the accuracy threshold is a second constant when the maximum value is less than the first initial threshold and greater than the second initial threshold, and wherein the accuracy threshold is determined from an empirical function when the maximum value is less than the second initial threshold, the empirical function providing the accuracy threshold based on the maximum value of the plurality of signal data points.

26. The method of claim 25, further comprising:
determining the empirical function by:
for each signal of a plurality of different maximum values of signals that are known to be positive:
performing iterations of a Monte Carlo simulation by convoluting the signal with noise exhibiting a statistical distribution, wherein a level of noise in each of the iterations is dependent on observed noise in the signal;
determining a respective accuracy measure of a respective high-order regression function for each of the iterations;
determining an average and a standard deviation of the respective accuracy measures; and determining an accuracy data point by subtracting the standard deviation times a scaling factor from the average; and fitting parameters of the empirical function to the accuracy data points to obtain the empirical function that provides an accuracy threshold for an input peak value of a signal.

27. The method of claim 1, further comprising:

performing a linear regression of the plurality of signal data points;

determining whether lower and upper bounds of a confidence interval of a slope of the linear regression include zero; and identifying the sample as negative when the lower and upper bounds of the confidence interval.

28. The method of claim 27, where the confidence interval is chosen to be 10%.

29. A computer product comprising a computer readable medium storing a plurality of instructions for controlling a computer system to perform operations for-detecting an analyte in a sample, the operations comprising:

collecting a plurality of background data points using a detector, the background data points collected during a background time interval;

initiating activation of the sample by an activation reagent;

collecting a plurality of signal data points of a flash luminescence signal associated with the sample using the detector, wherein the plurality of signal data points is collected during a signal time interval that is after the background time interval, wherein the signal time interval includes a portion of time after the sample is activated by the activation reagent;

computing a signal-to-background ratio using the plurality of background data points and the plurality of signal data points;

determining a regression function that fits the plurality of signal data points, wherein the regression function includes at least a second order polynomial;

computing an accuracy value of the regression function fitting the plurality of signal data points;

calculating a score by adjusting an accuracy term using a signal-to-background term, the accuracy term including the accuracy value, and the signal-to-background term including the signal-to-background ratio; and comparing the score to a classification threshold to determine a classification of whether the sample is positive or negative for the analyte.

30. A system for detecting an analyte in a sample, the system comprising:

one or more processors configured to:

collect a plurality of background data points using a detector, the background data points collected during a background time interval;

initiate activation of the sample by an activation reagent;

collect a plurality of signal data points of a flash luminescence signal associated with the sample using the detector, wherein the plurality of signal data points is collected during a signal time interval that is after the background time interval, wherein the signal time interval includes a portion of time after the sample is activated by the activation reagent;

compute a signal-to-background ratio using the plurality of background data points and the plurality of signal data points;

determine a regression function that fits the plurality of signal data points, wherein the regression function includes at least a second order polynomial;

compute an accuracy value of the regression function fitting the plurality of signal data points;

calculate a score by adjusting an accuracy term using a signal-to-background term, the accuracy term including the accuracy value, and the signal-to-background term including the signal-to-background ratio; and compare the score to a classification threshold to determine a classification of whether the sample is positive or negative for the analyte.

31. The method of claim 1, wherein the flash luminescence signal is generated by a reporter molecule produced by a transduction particle.

* * * * *